United States Patent [19]

Ohmori et al.

[11] Patent Number: 5,212,159

[45] Date of Patent: May 18, 1993

[54] ANTICATARACT COMPOSITION

[75] Inventors: Shinji Ohmori, Okayama; Kazumi Ogata, Toyonaka; Yoshimasa Abe, Akashi, all of Japan

[73] Assignee: Senju Pharmaceutical Co., Ltd., Osaka, Japan

[21] Appl. No.: 947,961

[22] Filed: Sep. 21, 1992

Related U.S. Application Data

[62] Division of Ser. No. 836,429, Feb. 18, 1992, abandoned.

[30] Foreign Application Priority Data

Feb. 27, 1991 [JP] Japan .................................. 3-119645

[51] Int. Cl.$^5$ ..................... A61K 37/00; A61K 31/22; A61K 31/13
[52] U.S. Cl. ...................................... 514/19; 514/546; 514/562; 514/912
[58] Field of Search ................... 514/19, 546, 562, 912

[56] References Cited

FOREIGN PATENT DOCUMENTS 63-8337   1/1988  Japan .
2-255624 10/1990  Japan .
3-48626   3/1991  Japan .
3-118334  5/1991  Japan .

*Primary Examiner*—Frederick E. Waddell
*Assistant Examiner*—Zohreh A. Fay
*Attorney, Agent, or Firm*—Wenderoth, Lind & Ponack

[57] ABSTRACT

The invention provides an anticataract composition containing a compound of the following formula $$\text{HOOC—CH—CH}_2\text{CH}_2\text{—CONH—CH—CONH—CH}_2\text{—COOH}$$
$$\quad\quad\quad | \quad\quad\quad\quad\quad\quad\quad\quad\quad\quad |$$
$$\quad\quad\text{NH}_2 \quad\quad\quad\quad\quad\quad\quad\quad \text{CH}_2\text{—S—CH—COOR}$$
$$\quad\quad\quad\quad\quad\quad\quad\quad\quad\quad\quad\quad\quad\quad |$$
$$\quad\quad\quad\quad\quad\quad\quad\quad\quad\quad\quad\quad\quad\quad \text{CH}_2\text{—COOR}$$

[wherein Rs are the same or different and each means a hydrogen atom or a lower alkyl group] or a pharmacologically acceptable salt thereof.

The anticataract composition of this invention is useful for the prevention and treatment of various types of cataract including senile cataract and diabetic cataract.

9 Claims, 2 Drawing Sheets

Days after the beginning of treatment (Day)

ANTICATARACT COMPOSITION

This application is a division of now abandoned application Ser. No. 07/836,429, filed Feb. 18, 1992, now abandoned.

BACKGROUND OF THE INVENTION

1. Field of the Invention

This invention relates to a useful anticataract composition. More particularly, the invention relates to a useful anticataract composition containing S-($\alpha,\beta$-dicarboxyethyl)glutathione, which is a substance found in the body, an ester derivative thereof or a pharmacologically acceptable salt thereof.

2. Description of the Prior Art

Cataract is a disease characterized by an opacification of the crystalline lens owing to various etiologic factors and includes, inter alia, senile cataract and cataract induced by drugs such as steroids.

Aside from the above, a diabetic tends to develop diabetic cataract as a typical complication if his general condition is left uncorrected for a long time. In extreme cases, cataract leads to blindness and requires a surgical intervention for recovery of vision.

Thus far, several anticataract drugs are known for the treatment of cataract due to various causes, such as senile cataract and diabetic cataract, but none have proved to be sufficiently satisfactory in, for example, efficacy.

The inventors of this invention accordingly explored for compounds having superior anticataract activity and found surprisingly that S-($\alpha,\beta$-dicarboxyethyl)-glutathione, which is a physiological substance, and its ester derivatives have very potent anticataract activity. This invention has been conceived and developed on the foundation of the above finding.

SUMMARY OF THE INVENTION

This invention is, therefore, directed to an anticataract composition containing a compound of the following formula

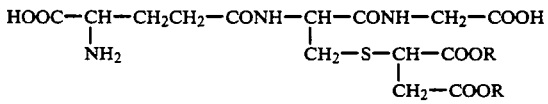

[wherein Rs are the same or different and each means a hydrogen atom or a lower alkyl group] or a pharmacologically acceptable salt thereof (hereinafter referred to briefly as the present compound) as an active ingredient.

DETAILED DESCRIPTION OF THE INVENTION

Of various species of the active ingredient for use in the anticataract composition of this invention, S-($\alpha,\beta$-dicarboxyethyl)glutathione is a physiological substance which D. H. Calam and S. G. Waley (Biochem. J. 86, 226 (1963)) first discovered in the bovine crystalline lens and the inventors of this invention previously discovered that this substance has blood anticoagulant activity, platelet aggregation-inhibitory activity, antiinflammatory/antiallergic activity, and hepatic impairment-inhibitory activity (Japanese Kokai Tokkyo Koho No. 63-8337, No. 1-79956, No. 1-183484 and No. 1-256370).

Referring to the above formula, Rs are the same or different and each means a hydrogen atom or a lower alkyl group which contains preferably 1 to 10 carbon atoms. The alkyl group may be straight-chain, branched or cyclic, and may even contain a ring structure. The alkyl group as such includes methyl, ethyl, n-propyl, i-propyl, cyclopropyl, n-butyl, t-butyl, sec-butyl, n-pentyl, 1-ethylpropyl, i-pentyl, benzyl and so on.

In the anticataract composition of this invention, the present compound can be used as the free acid or in the form of a pharmacologically acceptable salt such as an alkali metal salt, e.g. sodium salt, potassium salt, etc. or an alkaline earth metal salt, e.g. calcium salt, magnesium salt and so on. With regard to these salts, any and all of the carboxyl groups available in the present compound may be in the salt form and any of such salts can be conveniently used in the manufacture of the pharmaceutical composition of this invention. The number of carboxyl groups in the salt form in the present compound can vary depending upon the kind of salt and the pH condition of a manufacturing method employed.

According to the intended use and necessity, one or more suitable species of the active ingredient can be used in the anticataract composition of the invention.

The present compound to be used as an active ingredient of the anticataract composition of this invention can be made available by the following and other methods. Because S-($\alpha,\beta$-dicarboxyethyl)glutathione exists in yeasts, bovine crystalline lens and so on, it can be extracted from such materials and isolated in pure form by the known method. As to synthetic production processes, a typical procedure comprises starting with glutathione and allowing an equimolar mixture of glutathione and maleic acid in water or an alcoholic aqueous medium at ambient temperature or a slightly elevated temperature for 1 to 2 days to give S-($\alpha,\beta$-dicarboxyethyl)glutathione. A maleic acid monoester or a maleic acid diester can also be used in the same manner to give the corresponding S-($\alpha,\beta$-dicarboxyethyl)glutathione ester derivative. While the compounds thus obtained invariably have asymmetric carbon atoms and, hence, may show optical activity, any of such optical isomers as well as racemic mixtures thereof can likewise be used with advantage in the practice of this invention.

The present compound, which is used as an active ingredient of the anticataract composition of the invention, is a physiological substance found in the body or an ester derivative thereof. Therefore, it is only sparingly toxic, as will be seen from Example 2 which appears hereinafter, and can be safely used in a variety of dosage forms in the treatment of various types of cataract with advantage.

The anticataract composition of this invention can be administered, orally or otherwise, for the prevention or treatment of various types of cataract inclusive of senile cataract and diabetic cataract. Useful preparations include a variety of solid preparations, such as tablets, granules, powders, capsules, etc., or a variety of liquid preparations, such as eyedrops, injections and so on. These preparations can all be manufactured by the known pharmaceutical procedures. In the manufacture of such preparations, there can be used a variety of known excipients such as binders, disintegrators, thickeners, dispersants, reabsorption promoters, corrigents, buffers, surfactants, solubilizers, preservatives, emulsifiers, isotonizing agents, stabilizers, pH adjusting agents and so on.

The dosage of the present compound for purposes of the invention depends on species of the present compound, the patient's age and body weight, dosage form, clinical condition of the patient and other conditions. Taking an injectable preparation as an example, the recommended daily dosage for adults is about 1 to 100 mg, which is to be administered once a day. The oral dosage for adults is about 10 to 1,000 mg per dose to be administered a few times a day. In the case of eyedrops, the present compound can be administered in a dosing concentration of about 0.1 to 5 percent with a frequency of several times a day.

Unless contrary to the object of the invention, the anticataract composition of this invention may additionally contain one or more other anticataract agents and/or other medicinal ingredients.

EXAMPLE

The following experimental examples, synthesis examples and working examples are intended to describe this invention in further detail.

EXPERIMENTAL EXAMPLE 1

Inhibitory Effect on Streptozotocin-induced Diabetic Cataract

Method

Streptozotocin (hereafter abbreviated as STZ), 70 mg/kg, was administered intravenously to 28 male SD rats aged 4 weeks to induce diabetes. Thereafter, the animals were divided into three groups (two groups consisting of 10 animals each and a group consisting of 8 animals). One group received 2% glutathione (dissolved in physiological saline, hereafter referred to as GSH group), another group S-(diethyl α,β-carboxyethyl)glutathione sodium (dissolved in physiological saline, hereafter referred to as DCE-EtGS group), and a third group physiological saline (hereafter referred to as control group), all intraperitoneally in a volume of 0.5 ml/100 g body weight once a day for 56 days (100 mg/kg/day as active substance). The lens was examined with a slit lamp under mydriasis with Mydrin-P before the beginning of drug administration and every seven days after initiation of administration. The degree of cataract was scored according to the rating scale of Sasaki et al. (Ophthalmic Res. 15: 185–190, 1983) and the anticataract activity of each drug was tested by time series analysis of variance. Body weights were taken on each observation day. Incidentally, blood glucose levels were determined 5 days after administration of STZ and the study was continued only after confirmation of hyperglycemia.

Rating scale of Sasaki et al.
0: No abnormality.
1: Vacuoles are present in the equator of the lens.
2: Vacuoles spread toward the anterior pole beneath the cortex of the anterior lens capsule.
3: Vacuole begin to merge.
4: The deep layer of the cortex of the anterior lens capsule is cloudy.
5: The central part of the lens is milk white in color.
6: Virtually the entire lens is milk white in color (mature cataract).

Results

The scores at each time point of observation are shown in Table 1 and the mean scores in FIG. 1.

TABLE 1

Time Course of Cataract Score

| Days | Control | | | | | | | DCE-Et GS | | | | | | | Glutathione | | | | | | |
|---|---|---|---|---|---|---|---|---|---|---|---|---|---|---|---|---|---|---|---|---|---|
| | 0 | 1 | 2 | 3 | 4 | 5 | 6 | 0 | 1 | 2 | 3 | 4 | 5 | 6 | 0 | 1 | 2 | 3 | 4 | 5 | 6 |
| 0 | 20 | | | | | | | 20 | | | | | | | 16 | | | | | | |
| 7 | 11 | 9 | | | | | | 15 | 5 | | | | | | 7 | 9 | | | | | |
| 14 | 2 | 16 | 3 | | | | | | 20 | | | | | | 1 | 13 | 2 | | | | |
| 21 | | 3 | 17 | | | | | | 7 | 13 | | | | | | 3 | 13 | | | | |
| 28 | | | 11 | 9 | | | | | 2 | 10 | 8 | | | | | | 9 | 7 | | | |
| 35 | | | 4 | 15 | 1 | | | | 2 | 7 | 11 | | | | | | 3 | 8 | 3 | | |
| 42 | | | 4 | 11 | 4 | 1 | | | 2 | 5 | 11 | 2 | | | | | | 11 | 3 | | |
| 49 | | | | 11 | 3 | 5 | 1 | | | | 12 | 5 | 1 | | | | | 10 | 3 | 1 | |
| 56 | | | | 6 | 4 | 2 | 8 | | | | | 4 | 12 | 2 | | | | 4 | 6 | 3 | 1 |

Each figure represents the number of eyes.

Whereas the control group showed vacuolation in 45% of the eyes after 7 days, the DCE-EtGS group showed a vacuolation rate of only 25% and a slower progression of cataract, with the scores of 2, 4, 5 and 6 being reached later than in the control group. Time series analysis of variance in regard to the degree of progression of cataract showed a significant delay of progression in the DCE-EtGS group as compared with the control group. In the GSH group, vacuolation was noticed in 56.3% of all the eyes after 7 days and the scores of 5 and 6 were reached later than in the control group, although time series analysis of variance revealed no significant difference from the control group. It was, therefore, concluded that DCE-EtGS is effective in delaying the progression of cataract. The time courses of body weight during the treatment period are shown in FIG. 2. Body weight gain was also significantly greater in the DCE-EtGS group than in the control group. These results suggest the potential of DCE-EtGS to systemically alleviate diabetic complications.

EXPERIMENTAL EXAMPLE 2

Intravenous Acute Toxicity Study

An intravenous acute toxicity study of DCE-GS was conducted using 5 male ddY mice weighing about 20 g. The doses were 100, 200, 400, 800 and 1,600 mg/kg (common ratio 2). The dosing solutions were adjusted to pH 7 with 1N sodium hydroxide. Observation of the course over 72 hours after administration revealed no death or abnormal behavior at all.

SYNTHESIS EXAMPLE 1

S-(α,β-Dicarboxyethyl)glutathione

In 150 ml of water are dissolved 9.2 g of glutathione and 5.0 g of maleic acid and the solution is allowed to stand at room temperature for 12 hours. One or 2 drops of the reaction mixture is taken as a test sample and one drop of 0.01 N-iodine test solution (Japanese Pharmacopoeia XII) is added. After confirming that the consumption of iodine has ceased, 6.6 g of copper acetate (monohydrate) is added to the reaction mixture and dissolved and any precipitate is filtered off. The filtrate is concentrated to about 70 ml and diluted with ethanol and the precipitated blue copper salt is recovered by filtration and recrystallized from water-ethanol. This copper salt is dissolved in 200 ml of water and hydrogen sulfide is then bubbled through the solution to precipitate the copper sulfide which is then filtered off. The filtrate is concentrated under reduced pressure and diluted with ethanol and the resulting white crystals are collected by filtration, washed with ethanol and recrystallized from water-ethanol. Thus is obtained about 9 g of the title compound as white amorphous crystals (hygroscopic).

SYNTHESIS EXAMPLE 2

S-(α,β-dicarboxyethyl)glutathione sodium

In 40 ml of water is dissolved 2 g of S-(α,β-dicarboxyethyl)glutathione and the solution is adjusted to pH 7 with 1N-NaOH and concentrated under reduced pressure at a temperature not exceeding 30° C. The concentrate is diluted with ethanol and the resulting white crystals are collected by filtration and recrystallized from water-ethanol. Thus is obtained 2.1 g of the title compound as white powdery crystals.

SYNTHESIS EXAMPLE 3

S-(α,β-dicarboxyethyl)glutathione calcium

In 40 ml of water is dissolved 2 g of S-(α,β-dicarboxyethyl)glutathione followed by addition of 1 g of calcium carbonate. The mixture is stirred under warming. When the evolution of carbon dioxide gas has ceased, the excess of calcium carbonate is filtered off and the filtrate is concentrated under reduced pressure. To the concentrate is added ethanol and the resulting white crystals are collected by filtration and recrystallized from water-ethanol. Thus is obtained 2.2 g of the title compound as white powdery crystals.

SYNTHESIS EXAMPLE 4

S-(α,β-dicarboxyethyl)glutathione magnesium

Using 2 g of S-(α,β-dicarboxyethyl)glutathione and 1 g of basic magnesium carbonate, 2.2 g of the magnesium salt is prepared in a similar manner to the above production of the calcium salt.

SYNTHESIS EXAMPLE 5

S-(Diethyl α,β-dicarboxyethyl)glutathione sodium

In 150 ml of 30 (v/v) % ethanol are dissolved 9.2 g of glutathione and 5.6 g of diethyl maleate and the solution is adjusted to pH 6 with 2N sodium hydroxide solution. The solution is stirred at 50° C. for about 5 hours. Two drops of the reaction mixture are taken as a test sample and 1 drop of 0.01N iodine test solution (Japanese Pharmacopoeia XII) is added. After the iodine color has disappeared, hydrogen sulfide gas is bubbled through the solution, which is then allowed to stand overnight. The reaction mixture is then concentrated to remove hydrogen sulfide and the concentrate is dissolved in 150 ml of water. Then, 6.6 g of copper acetate (monohydrate) is added, whereupon a copper salt separates out gradually. The copper salt is recovered by filtration, rinsed and suspended in 150 ml of water, and hydrogen sulfide gas is then bubbled through the suspension to give copper sulfide. This copper sulfide is filtered off and the filtrate is concentrated. The concentrate is dissolved in 200 ml of ethanol and a solution of sodium hydroxide in ethanol is gradually added to bring the mixture to pH 6, whereupon white crystals separate out. These crystals are collected by filtration, washed with ethanol, dissolved in water and concentrated for recrystallization as much as possible. To the concentrate is added ethanol and the resulting crystals are collected by filtration and dried. Thus is obtained 8.5 g of S-(diethyl α,β-dicarboxyethyl)glutathione sodium. TLC, silica gel: Rf=0.28 (n-butanol:acetic acid:water=4:1:1).

SYNTHESIS EXAMPLE 6

S-(di-n-butyl α,β-dicarboxyethyl)glutathione sodium

In 150 ml of 50 (v/v) % ethanol are dissolved 9.2 g of glutathione and 7.5 g of di-n-butyl maleate and the reaction is conducted as in Synthesis Example 5. After the solvent is distilled off, the residue is dissolved in 150 ml of water followed by addition of 200 ml of 3.3% aqueous solution of copper acetate. The resulting insoluble copper salt is collected by filtration, rinsed and suspended in 300 ml of 50 (v/v) % ethanol. Then, hydrogen sulfide gas is bubbled through the suspension with stirring to give copper sulfide. This copper sulfide is filtered off and the filtrate is concentrated to remove hydrogen sulfide. The concentrate is redissolved in 150 ml of 50 (v/v) % ethanol, adjusted to pH about 6 with 2N-sodium hydroxide solution and concentrated. To the concentrate are added ethanol, acetone and isopropyl ether and the resulting white crystals are collected by filtration, washed with acetone and dried. Thus is obtained 9.7 g of S-(di-n-butyl α,β-dicarboxyethyl)glutathione sodium as hygroscopic crystals. TLC, silica gel: Rf=0.40 (n-butanol:acetic acid:water=4:1:1).

SYNTHESIS EXAMPLE 7

S-(Di-n-butyl α,β-dicarboxyethyl)glutathione calcium

The reaction and workup procedures of Synthesis Example 6 are repeated, using calcium carbonate in lieu of 2N-sodium hydroxide, and acetone is added to the concentrate to give white crystals. Recrystallization from ethanol-acetone yields 7.5 g of S-(di-n-butyl α,β-dicarboxyethyl)glutathione calcium.

SYNTHESIS EXAMPLE 8

S-(Monoethyl α,β-dicarboxyethyl)glutathione sodium

In 150 ml of water are dissolved 9.2 g of glutathione and 4.5 g of monoethyl maleate and the solution is adjusted to pH 6 with 2N-sodium hydroxide solution. The reaction is conducted in otherwise the same manner as in Synthesis Example 5. The reaction mixture is concentrated, the residue is diluted with ethanol and the resulting white crystals are collected by filtration, dissolved in water, concentrated and recrystallized from ethanol. Yield 8.0 g. TLC, silica gel: Rf=0.17 (n-butanol:acetic acid:water=4:1:1).

EXAMPLE 1

Ophthalmic Solution

| | |
|---|---|
| S-(Di-n-butyl α,β-dicarboxyethyl)glutathione sodium | 1.0 g |
| Boric acid | 0.7 g |
| Sodium chloride | 0.6 g |
| Methyl p-hydroxybenzoate | 0.02 g |
| Chlorobutanol | 0.3 g |
| Sodium hydroxide | q.s. |
| Sterile purified water | To make 100 ml |

EXAMPLE 2

Oral Tablet

| | |
|---|---|
| S-(Diethyl α,β-dicarboxyethyl)glutathione sodium | 100 mg |
| Lactose | 80 mg |
| Starch | 17 mg |
| Magnesium stearate | 3 mg |

The above ingredients per tablet are processed into tablets. The tablets may be sugar-coated, where necessary.

EXAMPLE 3

Injection

| | |
|---|---|
| S-(α,β-Dicarboxyethyl)glutathione sodium | 1.5 g |
| Sodium chloride | 0.6 g |
| Distilled water for injection | 100 ml |

The above ingredients are admixed and aseptically filtered. The filtrate is distributed in 2 ml portions into glass ampules which are then sealed by fusion to provide injections.

BRIEF DESCRIPTION OF THE DRAWINGS

In FIG. 1, ○ stands for DCE-EtGS treatment group, △ for glutathione treatment group, and ● for control group.

In FIG. 2, ○ stands for DCE-EtGS treatment group, △ for glutathione treatment group, and ● for control group. The symbols * and ** indicate significant differences from the control group; *: $p<0.05$ and **: $p<0.01$.

Figure 1:
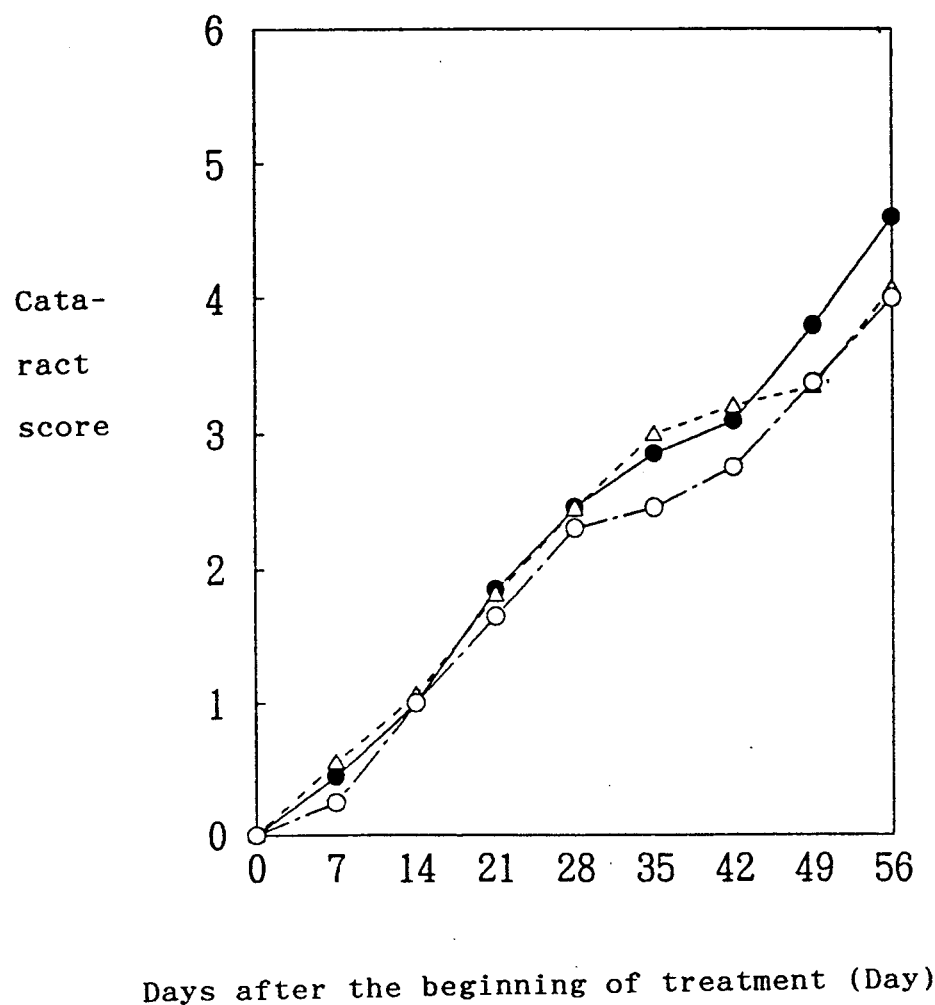
FIG. 1 shows the time course of mean score. The abscissa represents the time (in days) after the beginning of treatment and the ordinate represents the score.
Figure 2:
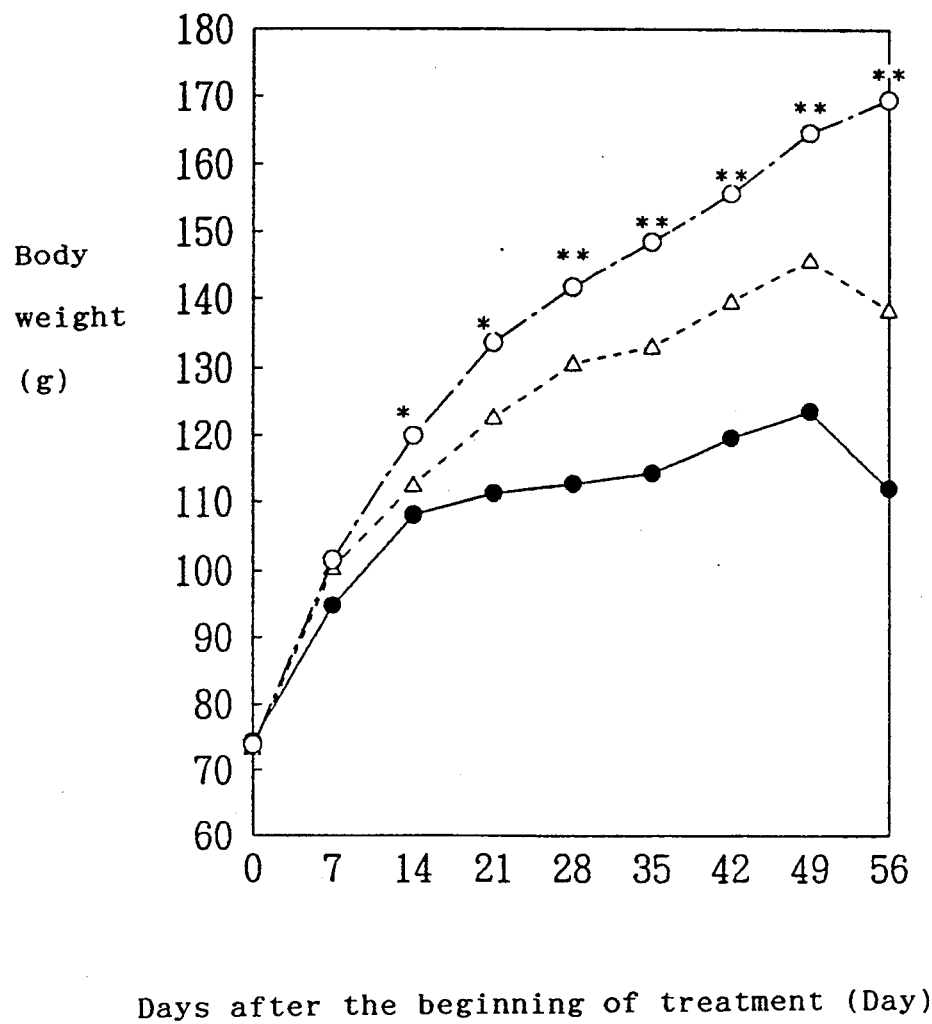
FIG. 2 shows the time course of mean body weight. The abscissa represents the time (in days) after the beginning of treatment and the ordinate represents body weight (g).

What is claimed is:

1. A method for the treatment of cataracts which comprises administering to a patient in need of such treatment an anticataract effective amount of a compound of the formula

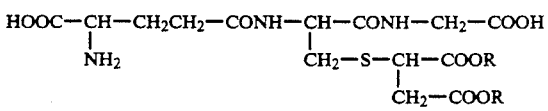

wherein the R groups are the same or different and each is a hydrogen atom or a lower alkyl group or a pharmacologically acceptable salt thereof.

2. A method according to claim 1, wherein the compound is S-(α-β-dicarboxyethyl)glutathione.

3. A method according to claim 1, wherein the salt is S-(α-β-dicarboxyethyl)glutathione sodium.

4. A method according to claim 1, wherein the salt is S-(α-β-dicarboxyethyl)glutathione calcium.

5. A method according to claim 1, wherein the salt is S-(α-β-dicarboxyethyl)glutathione magnesium.

6. A method according to claim 1, wherein the salt is S-(diethyl-α-β-dicarboxyethyl)glutathione sodium.

7. A method according to claim 1, wherein the salt is S-(di-n-butyl-α-β-dicarboxyethyl)glutathione sodium.

8. A method according to claim 1, wherein the salt is S-(di-n-butyl-α-β-dicarboxyethyl)glutathione calcium.

9. A method according to claim 1, wherein the salt is S-(monoethyl-α-β-dicarboxyethyl)glutathione sodium.

* * * * *